(12) United States Patent
Uphoff (10) Patent No.: US 6,245,063 B1
(45) Date of Patent: *Jun. 12, 2001

(54) APPARATUS FOR DECREASING OR ELIMINATING CURRENT LEAKAGES IN ELECTRO MEDICAL EQUIPMENT

(75) Inventor: Peter Uphoff, Denzlingen (DE)

(73) Assignee: Huettinger Medizintechnik GmbH & Co. KG, Umkirch (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/024,744

(22) Filed: Feb. 17, 1998

(30) Foreign Application Priority Data

| Feb. 17, 1997 | (DE) | 197 06 187 |
| Aug. 8, 1997 | (DE) | 197 34 369 |

(51) Int. Cl.$^7$ .................................................. A61B 18/04
(52) U.S. Cl. ................................................ 606/34; 606/32
(58) Field of Search .................. 606/32–35, 37–42, 606/45–50

(56) References Cited

U.S. PATENT DOCUMENTS

| 3,946,738 | * | 3/1976 | Newton et al. | 606/34 |
| 4,494,541 | * | 1/1985 | Archibald | 606/34 |
| 4,862,889 | * | 9/1989 | Feucht | 606/32 |
| 5,152,762 | * | 10/1992 | McElhenney | 606/35 |
| 5,300,070 | | 5/1994 | Gentelia et al. . | |
| 5,312,401 | * | 5/1994 | Newton et al. | 606/46 |
| 5,372,596 | * | 12/1994 | Klicek et al. | 606/35 |

FOREIGN PATENT DOCUMENTS

30 45 996   7/1982   (DE) .

* cited by examiner

Primary Examiner—Michael Peffley
(74) Attorney, Agent, or Firm—George H. Spencer; Robert Kinburg (57) ABSTRACT

An apparatus for an electrical surgical appliance is proposed, in which the undesirable leakage currents are considerably reduced or completely prevented. This is achieved according to the invention by a compensation circuit being provided, by means of which a compensation current can be produced in order to compensate at least partially for a leakage current at the neutral electrode.

5 Claims, 6 Drawing Sheets

APPARATUS FOR DECREASING OR ELIMINATING CURRENT LEAKAGES IN ELECTRO MEDICAL EQUIPMENT

FIELD OF INVENTION

The invention relates to an apparatus for reducing or preventing leakage currents in electrical medical appliances,

BACKGROUND OF THE INVENTION

Radio-frequency surgical appliances have a neutral electrode which makes contact with the patient to be treated, and have a so-called active electrode, which is used at the operation point. The radio-frequency current used for surgery flows from a generator, via the active electrode and through the patient's body and the neutral electrode back to the generator. As far as possible, the entire arrangement in modern RF surgical appliances is designed not to be grounded.

Nevertheless, in such an arrangement, a certain amount of leakage current always flows, both from the active electrode and from the neutral electrode, with respect to the ground potential. This is inevitably the case owing to the capacitances to ground potential that are always present. On the active electrode side, such capacitances which are, for example, in the form of a so-called ground capacitance from the output transformer and from circuit parts for monitoring and control in the output circuit as well as internal wires on the active electrode side, are on the order of magnitude of up to 100 pF or more. The connecting cable to the active electrode handpiece also has a ground capacitance on the order of magnitude of several tens of picofarads. On the neutral electrode side, a ground capacitance is formed from the output transformer and from circuit parts for monitoring as well as for internal wires on the neutral electrode side, and is on the order of magnitude of several tens of picofarads. Furthermore, the connecting cable for the neutral electrode in this case has a ground capacitance of several tens of picofarads, and the neutral electrode as well as the patient connected to it have a ground capacitance which may be up to several nanofarads.

The output voltage $U_{HF}$ from the said generator produces a ground current via the capacitances on the active electrode side, and this current flows back to the voltage source via the capacitances arranged on the neutral electrode side. Thus, leakage currents are also produced on the neutral electrode side itself, and these leakage currents represent a problem since the neutral electrode is connected directly to the patient, who is at a potential close to ground potential, as a result of which parasitic currents are possible whose profile cannot be defined exactly. Although, as a rule, the patients are supported such that they are insulated from ground potential, owing to his or her capacitance, the patient is very close to ground potential for a radio-frequency current. The insulated support merely reduces the risk of so-called current bottlenecks being formed at ground contact points, at which considerable heating can occur.

The leakage currents which are present owing to the ground capacitance of the patient may cause undesirable effects, and should thus be prevented if possible.

To this end, DE 27 40 751 has disclosed a safety circuit which produces an alarm if this leakage current exceeds a threshold value. This threshold value is itself controlled by a circuit so that fluctuations in the generator output power are compensated. However, this apparatus only allows the electrical surgical procedure to be terminated or interrupted as soon as the threshold value is exceeded and the undesirable leakage currents are too high.

Furthermore, DE 94 90 451 has disclosed an apparatus and a method by means of which the magnitude of the leakage currents is measured, and the output power of the radio-frequency generator is controlled. This apparatus thus represents active current limiting, although the current limiting may be restricted to the output power of the generator in such a way that the electrical surgical treatment is once again adversely affected.

In the past, so-called Type B appliances existed, in which the neutral electrode was solidly grounded. In this case, there were no leakage currents from the neutral electrode to ground, since they had already been shorted to ground in the appliance. However, this type of circuit results in a safety risk. If a defect occurs in another appliance connected to the patient, for example an EKG monitor, mains power could reach the patient, in the worst case, as a result of an insulation fault. This voltage with respect to ground would then lead to a lethally high current via the neutral electrode owing to the fact that the patient was directly grounded. This type of circuit is, (comma) therefore, (comma) no longer permissible and, instead of this, a capacitor is inserted in the ground line from the neutral electrode, which capacitor forms a negligible, low resistance for the RF current but limits the mains-frequency fault current to a safe level of max. 100 $\mu$A. Such appliances are called Type BF (body floating).

Such low-frequency currents are much too high for operations in the thorax region, so that appliances have been created in which the neutral electrode no longer has any direct ground reference. Such appliances are called Type CF (Cardial Floating) and are prior art in the OP field. In fact, there is now a problem here since the neutral electrode can assume an RF potential with respect to ground, as a result of which it is possible for leakage currents to flow on the neutral electrode side once again.

Undesirable leakage currents may occur not only when the described electrical surgical appliances are used but also in general with all electrical medical appliances.

SUMMARY OF THE INVENTION

The object of the invention is thus to propose a method and an apparatus in which the undesirable leakage currents in medico-technical appliances are considerably reduced, if not prevented completely, while the intention is to retain the safety of a so-called CF circuit.

This object is achieved as depicted in the drawings and the accompanying disclosure.

The measures cited in the dependent claims allow advantageous refinements and developments of the invention.

An apparatus as claimed in the invention is accordingly distinguished by the fact that a compensation device is provided by means of which a compensation current can be produced in order to compensate at least partially for a leakage current. This compensation current flows in the opposite direction to the undesirable leakage current so that, when the two currents are superimposed, the leakage current is at least drastically reduced, if not completely suppressed.

Particularly, (comma) in the case of a radio-frequency electrical surgical appliance having a generator, at least one active electrode and one neutral electrode, the negative effects mentioned above can thus be reduced or completely prevented without affecting operational safety.

In an advantageous development of the invention, a compensation voltage source is for this purpose connected to the neutral electrode on one side and to ground potential on the other side. The compensation current thus flows in the opposite direction to the leakage current, via the neutral electrode wire to ground, and back from ground to the compensation voltage source.

One particular embodiment of the invention also uses a compensation capacitance which is connected between the compensation voltage source and ground potential. It can be shown that, at least using such a compensation capacitance, complete compensation for the leakage currents is theoretically possible. This situation will be explained in more detail in the description of the exemplary embodiments.

Furthermore, it has been found to be advantageous for the compensation voltage to be substantially proportional to and/or in phase with the voltage which causes the leakage current, for example the output voltage from the radio-frequency generator in an electrical surgical appliance. On the other hand, complete compensation is made more difficult by the fact that the leakage current and the compensation current should, as far as possible, also be in phase and should be proportional to one another in order to achieve complete cancellation.

In a further particular embodiment of the invention, the compensation voltage is solidly coupled to the output voltage from the generator. Prom the design point of view, this permits particularly simple and thus cost-effective measures to be used to produce the compensation voltage source, particularly with regard to providing a compensation voltage which is in phase with the output voltage from the RF generator.

In one particular exemplary embodiment of the invention, the compensation current is regulated primarily by solidly coupling the compensation voltage to the output voltage via a so-called controllable attenuator and/or via a controllable compensation capacitance. In this way, even a fixed compensation voltage allows leakage currents to be trimmed down to a voltage which is as low as possible, and in the ideal case to be trimmed down to zero.

In a further particularly advantageous embodiment of the invention, the compensation voltage is tapped directly off the output transformer of the generator in an electrical surgical appliance, thus resulting in a particularly simple and cost-effective design and ensuring reliability, since the compensation voltage is in phase with the radio-frequency voltage from the generator. The compensation voltage may be tapped off the transformer via, for example, an additional winding and/or an additional transformer respectively on the primary and/or secondary side of the output transformer in the generator.

In a preferred development of the invention, the compensation capacitance is also integrated in a transformer housing, for example the output transformer of the radio-frequency generator in an electrical surgical appliance, from which the compensation voltage is also preferably tapped off. In one version, this can be achieved with particularly little complexity by forming a plate capacitor using a plate which is insulated from one wall of the housing. A flat piece of ceramic is preferably fitted between the transformer housing and the said capacitor plate, as the dielectric.

In order to control the compensation capacitance, the compensation capacitance is preferably mechanically controllable, for example being designed in the form of a variable plate capacitor. This may be driven, for example, via an electric motor, but an electromagnetic linear drive and/or a piezoelectric drive are also feasible without any problems.

All currently known or future options for designing a capacitance to be variable and controllable may be used in this context.

Based on a theoretical approach, a preferred method for compensating for leakage currents would also be to produce a so-called virtual ground point by means of a compensation amplifier. Using such a compensation amplifier, it is possible, for example, for the neutral electrode connection to be regulated at a ground potential, without any direct connection for the ground potential. This would completely prevent any leakage current flowing to ground. In this case, there would be no need for any additional regulator and any phase errors would be automatically compensated for by the amplifier. On the other hand, the dynamic requirements, particularly with regard to the bandwidth of such a power amplifier, are very stringent. However, particularly taking into account the further development of such amplifiers, it is nevertheless conceivable that cost-effective amplifiers having an appropriate power capability will be commercially available in the future. In this case, the use of such a power amplifier for the invention represents an extremely advantageous variant, as stated above.

Various exemplary embodiments of the invention are illustrated in the drawing and will be explained in more detail in the following text with reference to the figures.

DETAILED DESCRIPTION OF THE PREFERRED EMBODIMENTS

Figure 1:
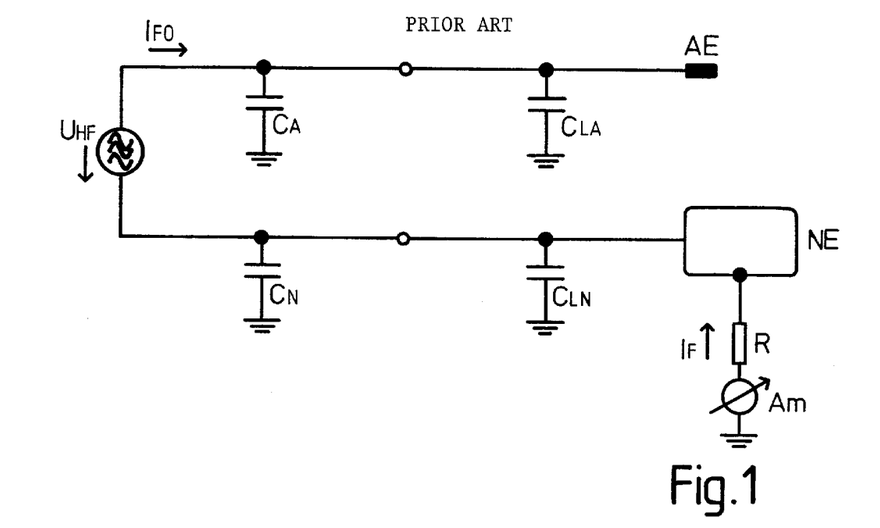
FIG. 1 shows a circuit for a surgical appliance according to the prior art, with a measurement circuit for a leakage current.

The circuit diagram according to FIG. 1 shows a radio-frequency voltage source $U_{HF}$ which is connected on the output side to an active electrode AE on one side and to a neutral electrode NE. The active electrode represents the actual hand-held instrument for the electrical surgical procedure. The neutral electrode is attached to the patient's body in order to close the circuit.

Undesirable parasitic capacitances on the active electrode AE side are represented by the capacitances $C_A$ and $C_{LA}$. The capacitance $C_A$ is in this case intended to represent the ground capacitance of the corresponding output of the output transformer and from circuit parts for monitoring and control, as well as that of the internal wire on the active electrode side. The capacitance $C_A$ is in the order of magnitude of several tens of picofarads.

A further capacitance results from the connecting cable for the handpiece, which is designated $C_{LA}$. This capacitance $C_{LA}$ may reach several tens of picofarads.

On the neutral electrode side, the ground capacitance of the corresponding output of the output transformer and from circuit parts for monitoring as well as that of the internal wires of the neutral electrode side are designated $C_N$. This capacitance may be several tens of picofarads Furthermore, the ground capacitance of the connecting cable for the neutral electrode, as well as the neutral electrode itself, are included in the circuit diagram under the designation $C_{LN}$. This capacitance may likewise be several tens of picofarads.

A measurement circuit for measuring the leakage currents is illustrated adjacent to the neutral electrode NE. A resistor R and a radio-frequency ammeter Am connect the neutral electrode to ground.

The internal output voltage $U_{HF}$ allows a current $I_{FO}$ to flow to ground via the capacitances $C_A$ and $C_{LA}$, and this current $I_{FO}$ flows back to the voltage source via the measurement path which comprises the resistor R and the ammeter Am and is connected to the neutral electrode. The proportion of this current which in the process flows back via the measurement path R, Am is the fault current $I_F$ on the neutral electrode side, which can be measured by the ammeter Am.

According to the invention, the aim is to reduce or completely suppress this fault current on the neutral electrode side.

Figure 2:
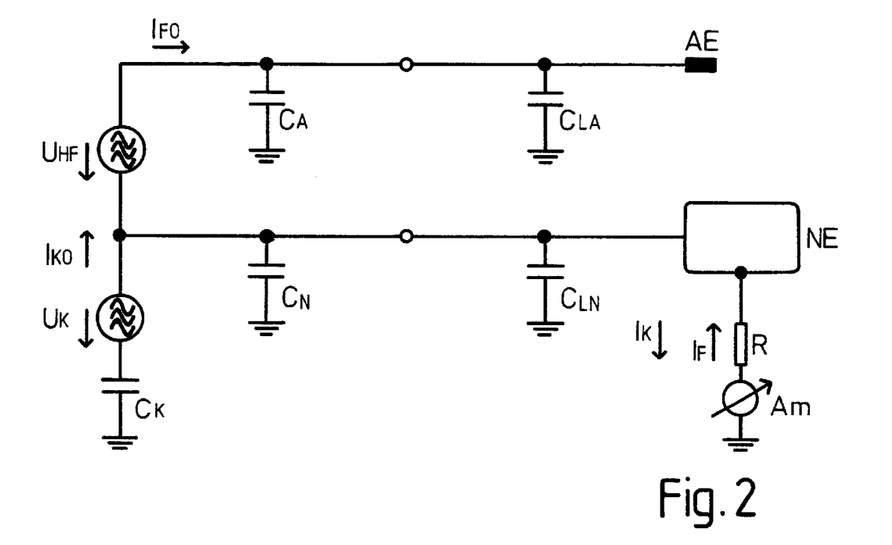
FIG. 2 shows an exemplary embodiment of a circuit according to FIG. 1, with an additional compensation voltage source.

According to the illustration in FIG. 2, a voltage source $U_K$ for compensation is installed for this purpose. This compensation voltage source $U_K$ is connected to the neutral electrode wire on one side and, via the compensation capacitor $C_K$, to ground on the other side. The compensation voltage source $U_K$ causes a compensation current $I_{KO}$ to flow. Part of this current flows via the capacitances $C_N$ and $C_{LN}$ back to the voltage source $U_K$. A further part of this compensation current $I_{KO}$ represents the compensation current $I_K$ which flows back via the neutral electrode and the measurement circuit R, Am. The current $I_K$ flows in the opposite direction to the fault current $I_F$. In order to provide optimum compensation for the fault current $I_F$, the compensation voltage source $U_K$ and the compensation capacitance $C_K$ must be designed appropriately.

Figure 3:
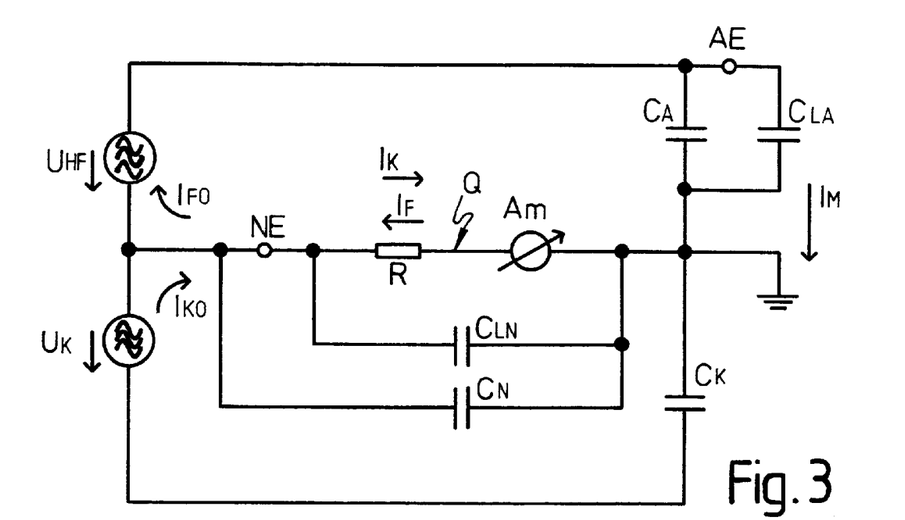
FIG. 3 shows the circuit diagram according to FIG. 2 illustrated in a different way.

In order to illustrate this design, the circuit according to FIG. 2 is illustrated in FIG. 3 in the form of a bridge circuit. The illustration according to FIG. 3, which corresponds exactly to FIG. 2, makes it evident that $I_K$ and $I_F$ must cancel one another out for complete compensation, that is to say they are of equal magnitude, but flow in opposite directions. In this case, there is no voltage drop across the lateral path Q. The following equations must apply in this situation;

$$I_{FO}=j\omega(C_A+C_{LA})U_{HF}$$

$$I_{KO}=j\omega C_K U_K$$

Furthermore, it is assumed that:

$$I_{FO}=I_{KO}$$

From the equations mentioned above, it follows that:

$$j\omega(C_A+C_{LA})U_{HF}=j\omega C_K U_K$$

The terms $j\omega$ on both sides cancel one another out in this case, leaving, as the condition for complete compensation, the equation:

$$C_K U_K=(C_A+C_{LA})U_{HF}.$$

The equations quoted above show that the fault current on the neutral electrode side can be compensated for completely, at least in theory. Furthermore, it can be seen from the above equations that this compensation can be carried out irrespective of the frequency and harmonic content of $U_{HF}$, as long as the term $j\omega$ is identical for both voltage sources $U_{HF}$ and $U_K$ and the two voltages are in phase.

The output voltage $U_{MF}$ from the radio-frequency generator as a rule has a variable magnitude. Thus, in order to comply with the conditions mentioned above, $U_K$ must vary in the same manner and in phase.

Even an appliance with fixed leakage current compensation would represent progress over the prior art since this would result in the leakage current on the neutral electrode side always being far enough away from the maximum limit value even for extreme cases of electrode connection line routing (and thus extreme parasitic capacitances). If this principle is extended to regulated compensation, then an appliance is obtained having characteristics that have never been achieved before. For example, there is no longer any risk whatsoever of a patient being burnt when the appliance is activated, as long as no operating current is flowing through the patient, even if this patient has direct ground contact, since the neutral electrode is kept at ground potential by the compensation, even though it is not connected to ground. It is at a so-called virtual ground potential.

No appliance interference whatsoever appears on the patient's monitors or on a video, provided no operating current is flowing through the patient. The bonding network is not affected by the surgical appliance.

In addition, output voltages of any required level may be used without the leakage current exceeding its maximum limit values.

A number of exemplary embodiments relating to regulated compensation are proposed in the following text.

Figure 4:
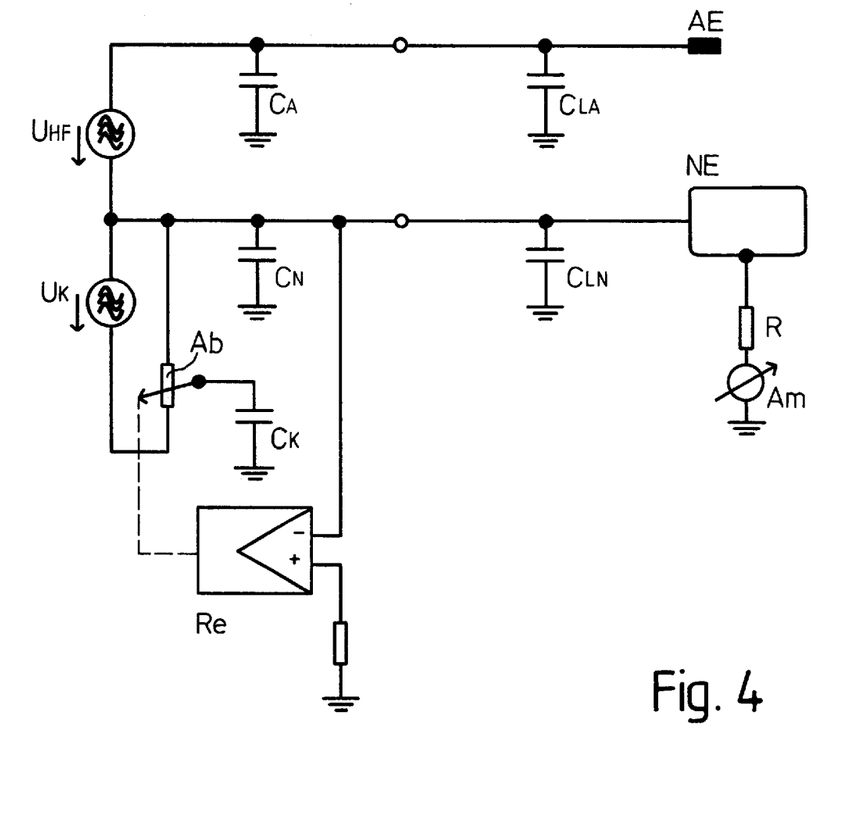
FIG. 4 shows an exemplary embodiment of the invention, with an attenuator used for regulation.

FIG. 4 illustrates the compensation voltage being regulated via a regulator Re and a so-called attenuator Ab. In the case of this control element, it is necessary to pay particular attention to ensure that no phase errors are produced. The attenuator Ab may be configured as a controllable resistor, for example in the form of a MOSFET transistor. The use of a power amplifier controlled via the generator voltage $U_{HFR}$ would also be feasible.

Figure 5:
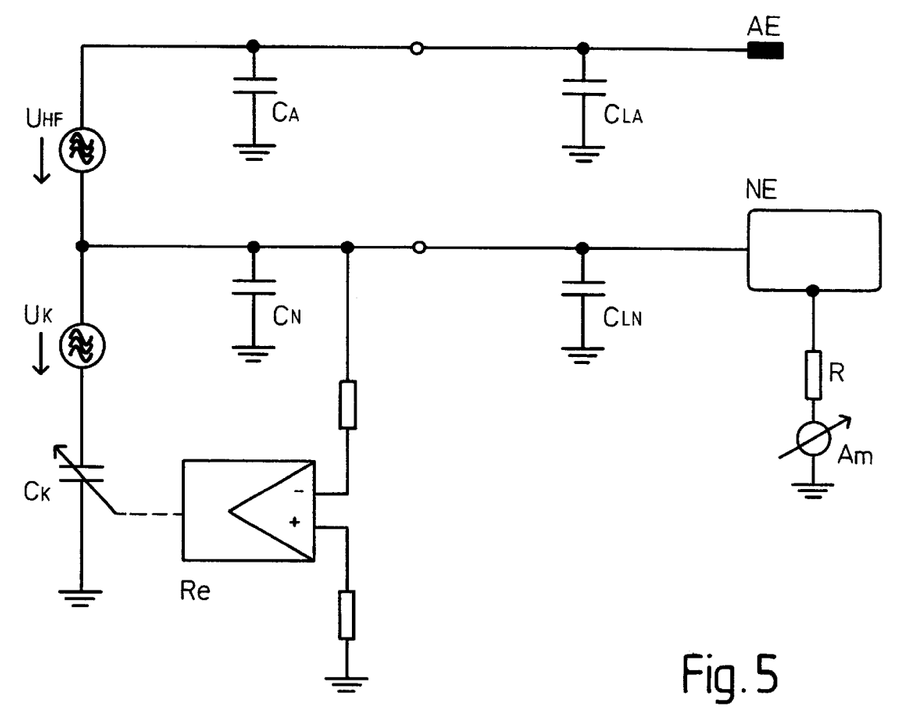
FIG. 5 shows a version of the invention in which the compensation capacitance is regulated.

In the illustration according to FIG. 5, the compensation capacitor $C_K$ is regulated via the regulator Re. The capacitor may in this case be designed to be mechanically constructed and mechanically variable. For example, a plate capacitor would be readily expedient. A drive element which can carry out a movement in the corresponding longitudinal range would be required as the control element This could be, for example, a piezoelectric element or the linear drive of a loud speaker. However, drive types using an electric motor or of some other type would also be feasible.

A flexible dielectric, such as an elastomer, could be used to produce the necessary dielectric strength. Depending on the drive used, this would provide a resetting element for the capacitor at the same time.

Figure 6:
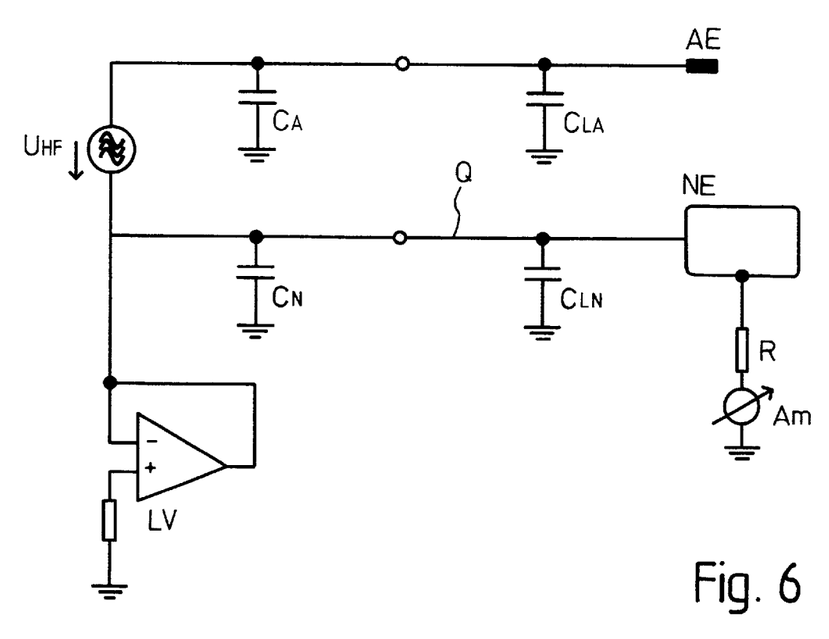
FIG. 6 shows an exemplary embodiment with a power amplifier.

The embodiment according to FIG. 6 once again shows a power amplifier used as a compensation voltage source. This compensation amplifier LV may be connected such that the output, on the neutral electrode side, from the output transformer $U_{HF}$ is always at ground potential. In consequence, no leakage current can flow through the transverse path Q. In this embodiment, there is no longer any need for a regulator, and any phase errors are compensated for automatically. However, as mentioned above, the dynamic requirements for such a power amplifier are very stringent.

As already mentioned above, in order to ensure that the compensation voltage $U_K$ is in phase with the output voltage $U_{HF}$ from the generator, it is expedient to tap the compensation voltage $U_K$ off directly from the output transformer in the generator.

Figure 7:
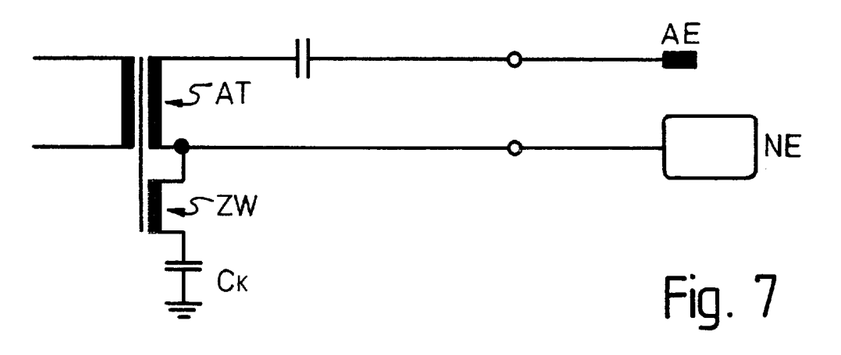
FIG. 7 shows an example for tapping off a compensation voltage by means of an additional winding on the output transformer of the radio-frequency generator.
Figure 8:
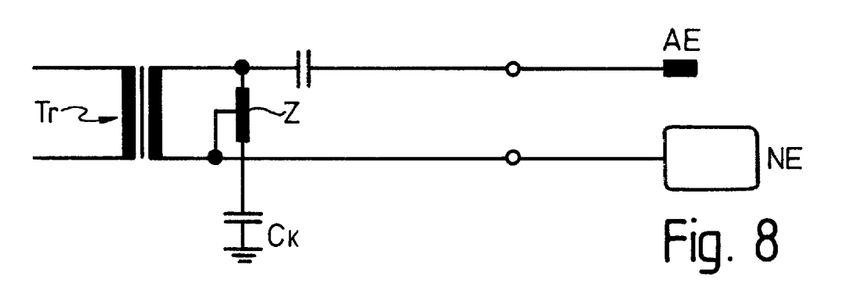
FIG. 8 shows an exemplary embodiment for tapping off the compensation voltage via an additional transformer on the secondary side.
Figure 9:
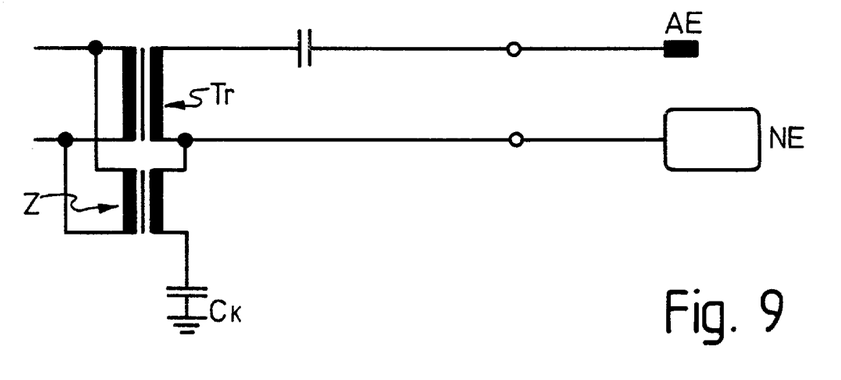
FIG. 9 shows an exemplary embodiment for tapping off the compensation voltage on the primary side of the output transformer.

FIGS. 7 to 9 show exemplary embodiments illustrating how such a voltage can be tapped off. In FIG. 7, an additional winding ZW is provided on the output transformer Tr. In FIG. 8, an additional transformer Z is fitted on the secondary side of the output transformer Tr. In FIG. 9, an additional transformer Z is arranged on the primary side of the output transformer Tr. In all these cases, a compensation voltage is obtained that is in phase with the generator voltage $U_{HF}$.

Figure 10:
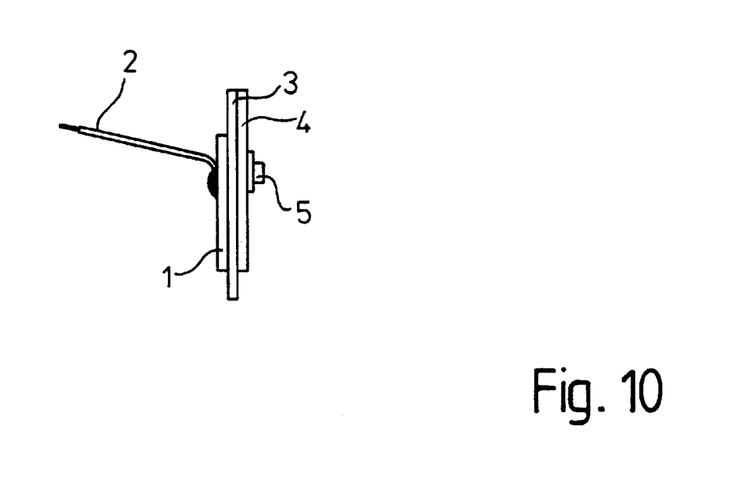
FIG. 10 shows an exemplary embodiment for the integration of a compensation capacitance in the housing of a transformer.

FIG. 10 illustrates a part of one housing wall 1 of a transformer housing. The transformer housing 1 has a terminal 2 for connection to the compensation voltage $U_K$, which can be tapped off directly from the output transformer in the radio-frequency generator. A ceramic sheet 3 is used as a dielectric between the housing 1 and an outer plate 4 made of metal. The outer plate 4 is preferably made of copper and is provided with a terminal 5, by means of which the outer plate 4 can be grounded. A capacitance $C_K$ is formed between the housing 1 and the outer plate 4 in the manner illustrated, so that the entire compensation circuit forms a unit which is installed with the output transformer of the radio-frequency generator. The configuration described and illustrated thus represents a particularly advantageous solution for production.

I claim:

1. An apparatus for suppressing leakage current in a radio-frequency electrical medical appliance comprising:

at least one active electrode connected and electrically coupled to said radio-frequency medical appliance;

a second electrode in contact with a patient;

a voltage source arranged between the active and second electrodes; and means for producing a compensation current to compensate, at least partially for a leakage current, said compensation current flowing in a direction opposite to said leakage current.

wherein said means for producing a compensation current includes means for regulation of said compensation current production means and said regulation means comprises a power amplifier controlled by voltage between the second electrode and ground.

2. The apparatus according to claim 1, wherein said means for producing a compensation current includes means for regulation of said compensation current production means, said regulation means configured so as to ensure that no phase errors are produced.

3. The apparatus according to claim 2, wherein said regulation means comprises:

a regulator; and an attenuator.

4. The apparatus according to claim 3, wherein said attenuator is a controllable resistor.

5. The apparatus according to claim 1, further comprising a compensation voltage source arranged between the second electrode and a ground.

* * * * *